US006489158B1

(12) United States Patent
Hendrick et al.

(10) Patent No.: US 6,489,158 B1
(45) Date of Patent: Dec. 3, 2002

(54) NON-LACTATE-ASSIMILATING YEAST FOR IMPROVING AEROBIC STABILITY OF SILAGE

(75) Inventors: Carol A. Hendrick, Des Moines, IA (US); Nancy J. Platt, Des Moines, IA (US); Barbara G. Ruser, Buxtehude (DE); Dean A. Hoganson, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/350,710

(22) Filed: Jul. 9, 1999

(51) Int. Cl.$^7$ .................................................. C12N 1/16
(52) U.S. Cl. ........................ 435/255.2; 435/267; 426/62
(58) Field of Search ............................ 435/255.2, 267; 426/62

(56) References Cited

U.S. PATENT DOCUMENTS

| 4,863,747 A | 9/1989 | Tomes .......................... 426/61 |
| 5,215,898 A | 6/1993 | Bolen et al. ................ 435/71.1 |

FOREIGN PATENT DOCUMENTS

WO    WO 97/29644    8/1997

OTHER PUBLICATIONS

Weinberg, Z.G., "New trends and opportunities in the development and use of inoculants for silage", *FEMS Microbiology Reviews* 19(1966) 53–68.

Kitamoto, Hiroko K., "Selection of killer yeasts (*Kluyveromyces lactis*) to prevent aerobic deterioration in silage making", *J. Dairy Sci.* (1993) 76:803–811.

*Primary Examiner*—Charles L. Patterson, Jr.
(74) *Attorney, Agent, or Firm*—Pioneer H-Bred International, Inc.

(57) ABSTRACT

A method for treating silage to enhance aerobic stability by inhibiting growth of yeast strains associated with spoilage of silage is disclosed. The method comprises treating silage or feed with a composition comprising killer yeast strains, or the antimicrobial components produced thereby. According to the invention, strains of *Saccharomyces exiguus* have been purified and isolated which are nontoxic, safe, do not assimilate lactate and which improve aerobic stability of silage, are disclosed. Portions of these strains have been sequenced to further characterize the invention.

21 Claims, 4 Drawing Sheets

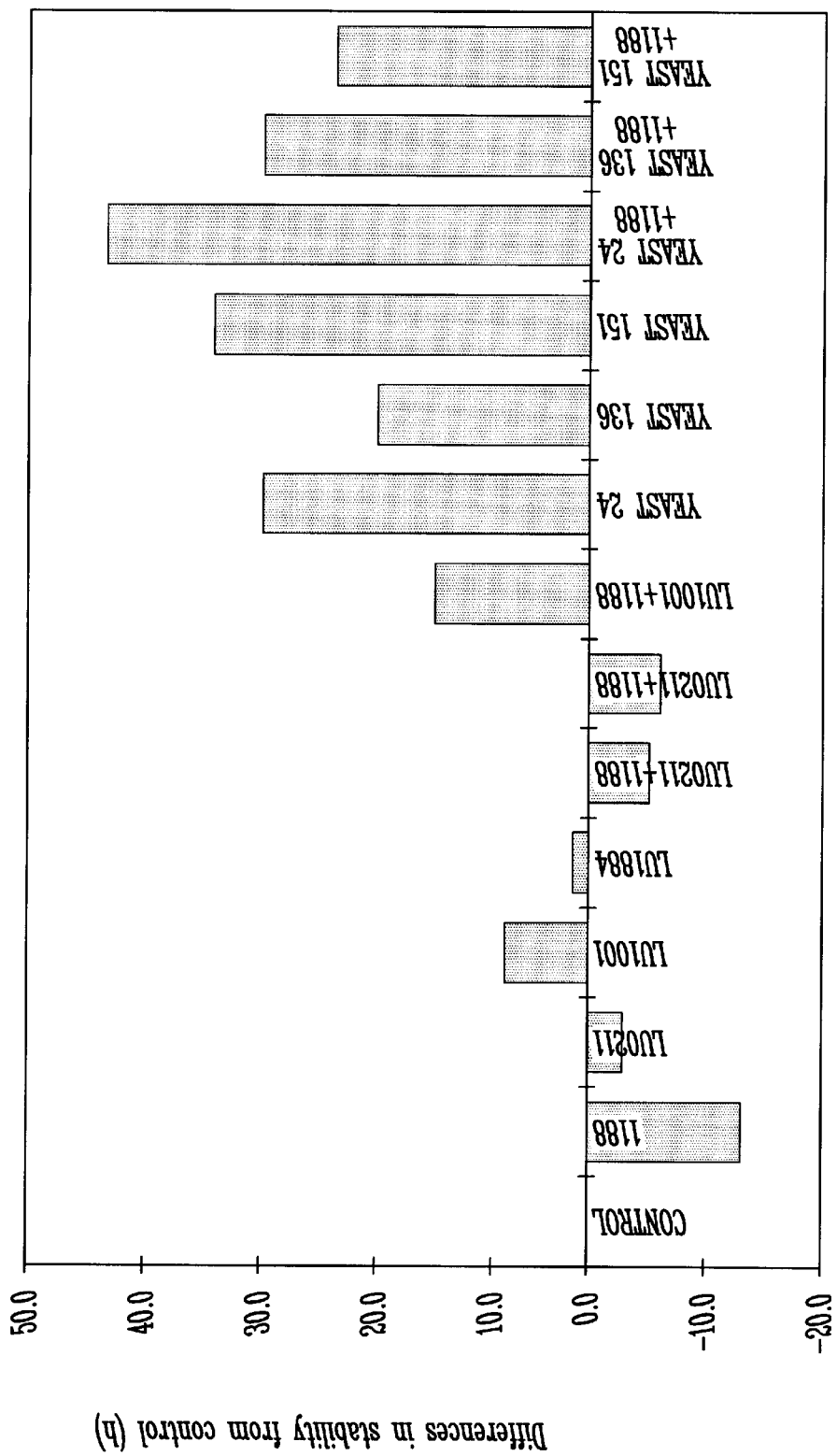

CONSENSUS > CTACGGAAACCTTGTTACGACTTTTAGTTCCTCTAAATGACCAAGTTTGTACAAATTCTC
CONSENSUS > CGCTCTGAGATGGAGTTGCCCCCTCCTCTAAGCAGATCCTGAGGCCTCACTAAGCCATTC
CONSENSUS > AATCGGTACTAGCGACGGGCGGTGTGTACAAAGGGCAGGGACGTAATCAACGCAAGCTGA
CONSENSUS > TGACTTGCGCTTACTAGGAATTCCTCGTTGAAGAGCAATAATTACAATGCTCTATCCCCA
CONSENSUS > GCACGACGGAGTTTCACAAGATTACCAAGACCTCTCGGCCAAGGTTAGACTCGCTGGCTC
CONSENSUS > CGTCAGTGTAGCGCGCGTGCGGCCCAgAACGTCTAAGGGCATCACAGACCTGTTAtTGCC

CONSENSUS > TCAAACTTCCATCGGCTTGAAACCGATAGTCCCTCTAAGAAGCGGACAACC.AGCAAATG
CONSENSUS > CTAGCACCACTATTTAGTAGGTTAAGGTCTCGTTCGTTATCGCAATTAAGCAGACAAATC
CONSENSUS > ACTCCACCAACT.AAGAACGGcCATGCACCACCACCCACAAAATCAAGAAAGAGCTCTCA
CONSENSUS > ATCTGTCAATCCTTATTGTGTCTGGACCTGGTGAGTTTCCCCGTGTTGAGTCAAATTAAG

CONSENSUS > CCGCAgGCTCCACTCCT GGTGGTGCCCTTCCGTCAATTCCTTTAAGTTTC.AgCCTTGC
CONSENSUS > GAcCATACTCCCCCCAgAAcCCAAAGACTTTGATTTCTCGTAAgGtGcCgAgTGGGTCAT
CONSENSUS > TAAAAAAACACCACCCGATCCCTAGTCGGCATAGTTTATGGTTAAGACTACGACGGyATC
CONSENSUS > TGATCATCTTCGATCCCcTAACTTTCGTTCTTGATTAATGAAAACGTCCTTGGCAAATGC
CONSENSUS > TTTCGCAGTAGTTAGTCTTCAATAAATCCAAGAATTTCACCTCTGACAATTGAATACTGA
CONSENSUS > TGCCCCGACCGTCCcTATTAATCATTACGATGGTCcTAGAAACCAACAAAATAGAACCA
CONSENSUS > AACGTCCTATTCTATTATTCCATGCTAATATATTCGAGCAATACGCCTGCTTTGAACACT

CONSENSUS > CTAATTTTTTCAAAGTAAAAATCCTGGTTCGCCAAGAGCCACAAGGACCCAAGGTTAGCC
CONSENSUS > AGAAGGAAAGGTCCGCTTGGGATTCCAGTACACGAAAAAATCGGACCGGCCAAACAGACC
CONSENSUS > CAAAGTTCAACTACGAGCTTTTTAACTGCAACAACTTTAATATACGCTATT.GGAGCTGG
CONSENSUS > AATTACCGCGGCTGCTGGCACC.AGACTTGCCCTCCAATTGTTCCTCGTTAAGGtAtTTA
CONSENSUS > CATTGTACTCATTCCAATTACAAGACCCGAATGGGcCCTGTATCGTTATTTATTGTCACT

*Fig. 3A*

CONSENSUS > ACCTCCCTGAATTAGGATTGGGTAATTTGCGCGCCTGCTGCCTTCCTTGGATGTGGTAGC

CONSENSUS > CGTTTCTCAGGCTCCCTCTCCGGAATCGAACCCTTATTCCCCGTTACCCGTTGAAACCAT

CONSENSUS > GGTAGGCCACTATCCTACCATCGAAAGTTGATAGGGCAGAAATTTGAATGAACCATCGCC

CONSENSUS > AGCACAAGGCCATGCGATTCGAAAAGTTATTATGAATCATCAAAGAGTCCGAAGACATTG

CONSENSUS > ATTTTTTATCTAATAAATACATCTCTTCCGTaAGGTCGAGATTTTAAGCATGTATT.AgC

CONSENSUS > TCTAGAATTACCACAGTTATACCATGTAGTAA.AGGAACTATCAAATAAACGATAACTGA

CONSENSUS > TTTAATGAgCCATTCGCAGTTTCACTGTATAAATTGCTTATACTTAGACATGCATGGCTT

CONSENSUS > AATCTTTGAGACAAGCATATGACTACTGGCAGGATCAACCAGGT

*Fig. 3B*

NON-LACTATE-ASSIMILATING YEAST FOR IMPROVING AEROBIC STABILITY OF SILAGE

FIELD OF THE INVENTION

This invention relates generally to the silage process, to microorganisms, and use of the same in treating animal feed and silage to enhance aerobic stability, thus preventing spoilage.

BACKGROUND OF THE INVENTION

The ensiling process is a method of moist forage preservation and is used all over the world. Silage accounts for more than 200 million tons of dry matter stored annually in Western Europe and the United States alone. The concept involves natural fermentation, where lactic acid bacteria ferment water soluble carbohydrates to form organic acids under anaerobic conditions. This causes a decrease in pH which then inhibits detrimental microbes so that the moist forage is preserved. The process can be characterized by four different phases.

Upon sealing in the storage unit, the first phase is aerobic, when oxygen is still present between plant particles and the pH is 6.0 to 6.5. These conditions allow for continued plant respiration, protease activity and activity of aerobic and facultative aerobic microorganisms.

The second phase is fermentation which lasts several days to several weeks after the silage becomes anaerobic. Lactic acid bacteria develop and become the primary microbial population thereby producing lactic and other organic acids, decreasing the pH to 3.8 to 5.0.

The third phase is stable with few changes occurring in the characteristics of the forage so long as air is prevented from entering the storage unit.

The final phase is feedout when the silage is ultimately unloaded and exposed to air. This results in reactivation of aerobic microorganisms, primarily yeast, molds, bacilli and acetic acid bacteria which can cause spoilage.

Aerobic instability is the primary problem in silage production. Even before storage units are open for feedout, silage can be exposed to oxygen because of management problems (i.e., poor packing or sealing). Under these types of aerobic conditions, rapid growth of yeast and mold cause silage to heat and spoil, decreasing its nutritional value.

Aerobic instability can be a problem even in inoculated silage that has undergone what would traditionally be considered a "good" fermentation phase, namely a rapid pH drop, and a low terminal pH. The yeast which contribute to instability in these conditions may be those which are tolerant of acid conditions and can metabolize the lactic acid produced by lactic acid bacteria during fermentation.

Management techniques that can be used to help prevent this condition involve using care to pack the silage well during the ensiling process and, also, using care in removing silage for feeding to minimize the aeration of the remaining silage.

Management (compaction, unloading rates) largely affects the movement of oxygen into silage. During feedout, air can penetrate 1 to 2 m behind the silage face so that exposure to oxygen is prolonged. Fermentation acids and pH inhibit the rate of microbial growth, but spoilage rates are affected also by microbial numbers and the rate of aerobic microbial growth on available substrates.

It is possible to use both chemical and biological additives in making silage to promote adequate fermentation patterns especially under sub-optimal conditions. Biological additives comprise bacterial inoculants and enzymes. Bacterial inoculants have advantages over chemical additives because they are safe, easy to use, non-corrosive to farm machinery, they do not pollute the environment and are regarded as natural products. Silage inoculants containing principally homofermentative lactic acid bacteria have become the dominant additives in many parts of the world. Their function is to promote rapid and efficient utilization of a crop's water soluble carbohydrates resulting in intensive production of lactic acid and a rapid decrease in pH. Inoculants also reduce aerobic spoilage and improve animal performance.

Several problems, however, with lactic acid bacteria inoculants have been encountered. These problems primarily include failure to dominate fermentation and failure to inhibit adverse microbial activity. Other problems associated with lactic acid bacteria inoculants include infection by phage, failure to grow well on certain crops, bacteria not being viable at the time of application, and the epiphytic nature of the lactic acid bacteria population. Because these types of homofermentative lactic acid bacteria inoculants do not always prevent or reduce undesirable microbial activity, several new approaches have been tried.

A review of the silage process and the use of inoculants can be found in FMS Microbiology Rev. 19 (1996) 53–68, Weinberg, ZNG., and Muck, R E, "New trends and opportunities in the development and use of inoculants for silage", the disclosure of which is incorporated herein by reference.

The concept of heterofermentative lactic acid bacteria in an inoculant has gained recent favor. The idea is that increased levels of undissociated volatile fatty acids, such as acetate, may inhibit other microbes that initiate aerobic deterioration. Heterofermenters have the ability to convert lactic acid to acetic acid in the presence of oxygen, and the acetate produced may inhibit other deleterious organisms. With such a mechanism, one-third of the lactic acid dry matter consumed will be lost as carbon dioxide. However a small loss of 1% or perhaps up to 2% dry matter may easily offset much larger losses by aerobic microorganisms. Concerns with heterofermentative lactic acid bacteria include effects on animal performance as well as the identification of appropriate strains useful for the procedure. Different strains of even the same species do not have identical properties and vary in their fermentation characteristics.

PCT publication WO 97/29644 discloses a single strain of *Lactobacillus buchneri* (NCIMB 40788) which was found to inhibit the growth of spoilage organisms in the storage of silage. Other attempts to identify heterofermentative organisms for silage inoculants have included (Wyss et al., 1991, "Einfluss von Luftstress und die Wirkung von spezifishen Zusatzen anf die arobe Stabilitat von Grasswelksilagen", Wirschaftseigene Futter, 37: 129–141), which used an inoculant comprising lactate and propionate producing organisms in wilted grass silage. Weinberg et al. (1995), "The effect of a propionic acid bacterial inoculant applied at ensiling, with or without lactic acid bacteria on the aerobic stability of Pearl-Millet and maize silages", *J. Appl. Bacteriol.*, 78:430–436 disclosed the use of *Propionibacterium shermanii* in millet, corn, sorghum, and wheat silages. Propionic acid was produced only in a wheat silage in which the pH decline was delayed and thus aerobic stability was improved. In all other silages the pH decline was rapid and the propionic acid bacteria could not proliferate.

Another attempt included select strains of *Serratia rubidaea* and *Bacillus subtilis* along with *L. plantarum*. When used in bale grass silages the number of molds decreased significantly. Some improvement was also observed in high moisture ear corn. (Moran et al., (1993), "The development of a novel bacterial inoculant to reduce mold spoilage and improve the silage fermentation in big bale silage. In: *Silage Research* 1993, *Proceedings of the Tenth International Conference on Silage Research* (O'Kiely, P., O'Connell, M. and Murphy, J., Eds.) pp. 85–86, Dublin City University, Ireland). A similar composition to that for bale grass silage was developed for wheat silage which added Pediococcus strains to the composition. Pediococcus is capable of fermenting pentose sugars which result from hemicellulose hydrolysis in wheat silages. In a single trial with wheat silage, no improvement in the aerobic stability was observed.

The ensiling process is a complex one and involves interactions of numerous different chemical and microbiological processes. Further, different silages and different methods of ensiling present a variety of different needs. As can be seen a need exists in the art for further improvement in compositions and methods to improve the aerobic stability of silage.

It is an object of the present invention to provide a method and composition which can be used as an inoculant to improve aerobic stability of silage.

It is yet another object to provide novel yeast strains which can be used in compositions for improving aerobic stability.

It is a further object of the present invention to increase dry matter recovery of silage by reducing aerobic spoilage.

It is yet another object of the invention to provide an inoculant which is safe and nonhazardous for an additive to silage.

It is a further object of the invention to provide a natural additive composition for silage.

It is yet another object of the invention to provide quality silage material as determined by temperature, pH, dry matter recovery, nitrogen profile, color and microorganism count.

Other objects of the invention will become apparent from the description of the invention which follows.

SUMMARY OF THE INVENTION

According to this invention, forage materials which are to be stored are treated with particular yeast strains ("killer" yeast) which inhibit the growth of wild yeasts that cause aerobic deterioration. These yeast strains also do not utilize lactate thus further preserving forage quality and inhibiting or retarding aerobic deterioration.

The invention provides a method of treating forage materials to enhance their preservation which comprises administering to the forage materials an effective amount of a killer yeast strain, its functional equivalents, or the forage preserving, or cytotoxic compositions produced thereby. According to the invention several strains of microorganisms have been identified from 18S rRNA sequencing to be from the class Saccharomyces exiguus, namely SE24, SE136 and SE151 which have been deposited with the ATCC, accession numbers 74441, 74442, 74443 respectively. Any one of these strains or any combination of the same may be used according to the invention.

As explained in more detail below, the microorganisms of the invention have a unique effect, different from and/or extending beyond their non lactate assimilation. The organisms produce antimicrobial factors likely proteinacious which are characterized by their ability to inhibit the growth of other yeast strains associated with the spoilage of silage or a variety of other spoilage organisms.

These substances may be isolated and purified by methods known to those of ordinary skill in the art. As such, the substances themselves may be used directly to treat animal feed or silage. In other words, it may not be necessary to use a microorganism as such in the compositions and methods of this invention.

DETAILED DESCRIPTION OF THE FIGURES

FIG. 2 is a graph depicting the pooled result of four trials with inoculated whole plant corn silage. The silage treated with the yeast strains of the invention alone or in combination with 1188 had 20 to 45h higher aerobic stability than 1188 control treatments.

FIG. 3 is the 18S rRNA sequence of the yeast strains of the invention.

DETAILED DESCRIPTION OF THE INVENTION

Figure 1:
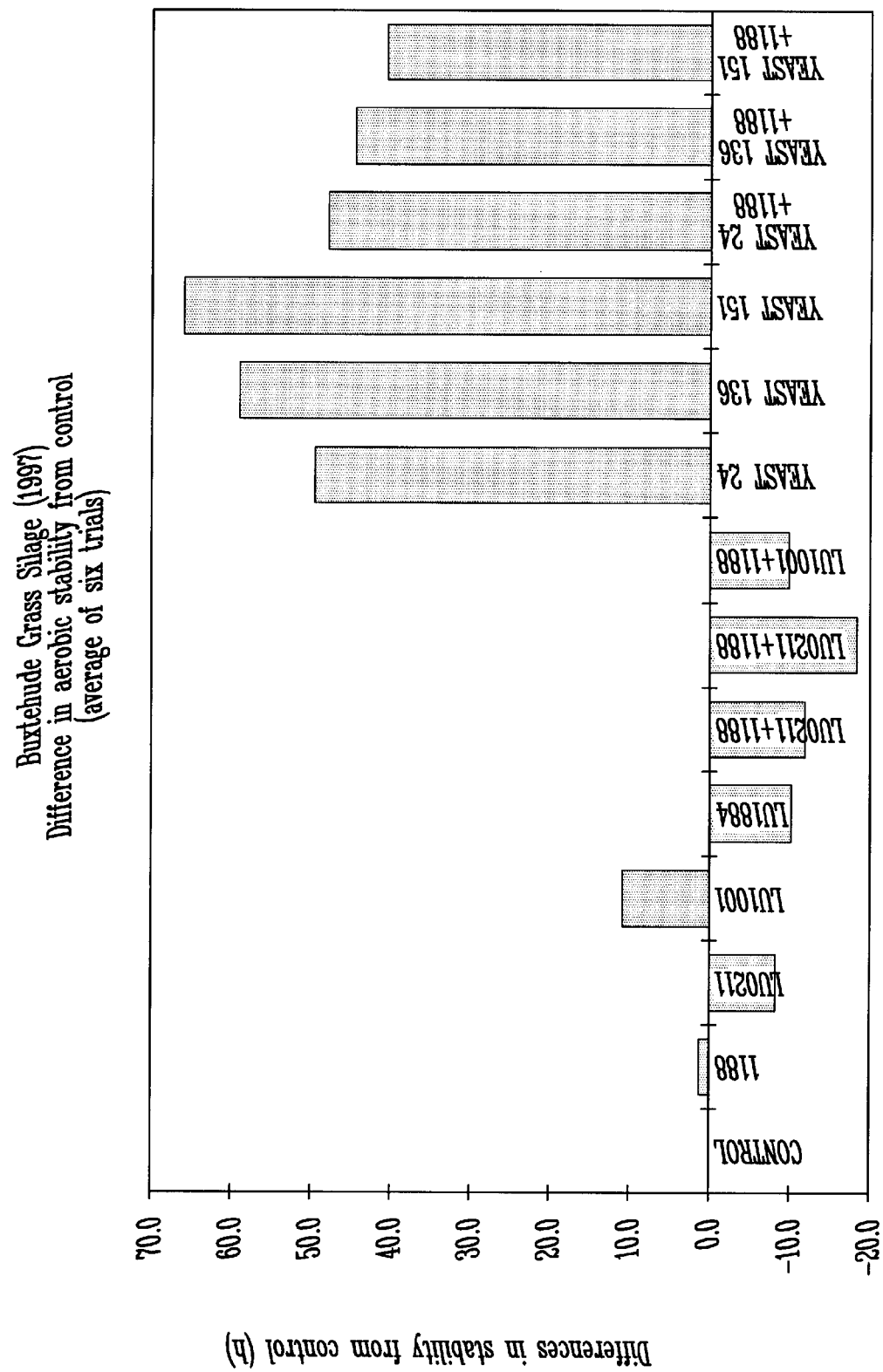
FIG. 1 is a graph depicting the pooled result of six grass forage trails. According to the results the yeast strains of the invention either alone or in combination with 1188 improved aerobic stability 35–60h over 1188, control and other bacterial inoculant treatments.

According to the invention microorganisms have been isolated and purified which improve the aerobic stability of ensued forage. Specific "killer yeast" strains have been identified which do not assimilate lactate and which inhibit growth of other yeast strains associated with the spoilage of silage. Three strains have been identified, SE24, SE136, and SE151 which from 18SrRNA sequencing indicate that they are Saccharomyces exiguus. These strains have been deposited with the ATCC with accession numbers 74441, 74442, and 7443 respectively. Further, the 18S rRNA region that each of these strains have in common has been sequenced helping to identify other strains which will likely exhibit similar activity. As used herein the term "substantially equivalent" shall mean a nucleotide sequence with from about 80–99.9% complementarity or homology to the sequence herein, with at least 90% complementarity or homology being preferred, as determined by methods known in the art and shall also include those sequences which will hybridize to the sequence in question in 7% sodium dodecyl sulfate (SDS), 0.5M $NaPO_4$ pH. 7.0, 1 mM EDTA at 50° C. and washing with 1% SDS at 42° C.

Unless otherwise stated, sequence identity/similarity values provided herein refer to the value obtained using the BLAST 2.0 suite of programs using default parameters. Altschul et al., *Nucleic Acids Res.* 25:3389–3409 (1997). Software for performing BLAST analyses is publicly available, e.g., through the National Center for Biotechnology Information (http://www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 3, an expectation (E) of 10, and the BLOSUM62 scoring matrix (see Henikoff & Henikoff (1989) *Proc. Natl. Acad. Sci. USA* 89:10915).

Further preferred embodiments of the invention are polynucleotides that are greater than 79%, preferably at least 80%, more preferably at least 85% identical to a polynucleotide of the invention. Among these particularly preferred polynucleotides, those with at least 90%, 95%, 98%, or at least 99% are especially preferred.

In the present invention, the inhibition of organisms responsible for spoilage is accomplished by treating the silage with organisms of the species *Saccharomyces exiguus*, especially the strains SE24, SE136, SE151 or with compositions containing these strains either alone or in combination or closely related organisms, and as well by treatment with effective mutants or equivalents of SE24, SE136, SE151 and compositions containing same.

The compositions which are used in the method of the invention may be in either liquid or dry form and may contain additional bacterial strains. In solid treatment forms, the composition may comprise the *Saccharomyces exiguus* together with a carrier. The carrier may be in the nature of an aqueous or nonaqueous liquid or a solid. In solid forms, the composition may contain solid carriers or physical extenders. Examples of such solid carriers, solid diluents or physical extenders include malto-dextrin, starches, calcium carbonate, cellulose, whey, ground corn cobs, and silicone dioxide. In short, the carrier may be organic or an inorganic physical extender. The solid composition can be applied directly to the forage in the form of a light powder dusting, or if it is disbursed in a liquid carrier it can successfully be sprayed on the forage.

Typical compositions useful for treating silage according to this invention contain $10^2$–$10^{12}$ viable organisms/gm, preferably $10^7$–$10^{10}$ viable organisms/gm, and more preferably $10^9$–$10^{10}$ viable organisms/gm in soluble formulations. For granular formulations preferred is $10^4$–$10^{10}$ and most preferred is $10^7$–$10^8$.

The treatment range for silage is typically $10^7$–$10^{17}$ viable organisms/ton, preferably $10^9$–$10^{15}$ viable organisms/ton, and more preferably $10^{10}$–$10^{12}$ viable organisms/ton.

Those of ordinary skill in the art will know of other suitable carriers and dosage forms, or will be able to ascertain such, using routine experimentation. Thus the strains can be used singly or in combination to determine a silage quality preserving amount of microorganisms or to determine the toxic effect generated from fermentation of the strains. Further, the administration of the various compositions can be carried out using standard techniques common to those of ordinary skill in the art.

As used herein the term "strain" shall be interpreted to include any mutant or derivative of strains SE24, SE136, SE151 deposited with the ATCC as accession numbers 74441, 74442, 74443, which retain the functional activity of improving aerobic stability of forage as described and defined by the methods and examples disclosed herein, with a typical increase of stability of from about 13–51 hours longer than control, or an increase in aerobic stability of approximately 1 to approximately 10% less aerobic loss.

The microorganisms of the invention were purified and isolated from grass silage. After much experimentation it was discovered from testing hundreds of isolates.

After purification and isolation of the specific strains, taxonomic studies and rRNA sequencing were done to identify the strains. They were identified as Saccharomyces exiguus and given the prototype numbers SE24, SE136, and SE151. According to the invention, these strains, compositions comprising these strains, or the cytotoxic factors produced by these strains, are used to treat forage materials.

Materials that are suitable for ensiling or storage, according to the methods of the invention, are any which are susceptible to aerobic spoilage. The material will usually contain at least 25% by weight dry matter. Such materials include rye or traditional grass, maize, including high moisture corn, whole plant corn, Lucerne, wheat, legumes, sorghum, sunflower, barley or other whole crop cereals. The silage may be in bales (a form particularly susceptible to aerobic spoilage), oxygen limiting bags, bunkers, upright stave silos, oxygen limiting silos, bags, piles or any other form of storage which may be susceptible to aerobic spoilage. Alternatively, the invention may be used with any susceptible animal feed, whether solid or liquid, e.g. for pigs, poultry or ruminants.

The activity associated with this invention may be found in other yeast strains of *S. exiguus* and possibly also in other genera. This can be established by routine experimentation, on the basis of the information herein.

EXAMPLES

Example 1

Buxtehude Grass Silage Trials

An experiment was conducted to inoculate grass forage with yeast having "killer" activity as well as bacteria that exhibit anti-yeast activity in bench-top assays, to determine whether aerobic stability of the silage is improved.

Methods

Trials were carried out in Buxtehude, Germany, by the standard methods used in European silage research studies (see Example 3). Grass was chopped and ensiled at 32–44.6% dry matter. PVC silos 4"×14" were used with a compaction rate of approx. 100 kg dry matter/m3 and two 48 hr periods of air infusion at 4 and 6 weeks post-ensiling. There were six locations and two replicate silos per treatment per opening day. Total yeast counts were determined by plating on Saboraud dextrose agar and lactate-assimilating yeast were determined by plating on Yeast Nitrogen Base Agar +1% sodium lactate. Volatile fatty acids (VFAs) and ethanol were determined on silage extracts by HPLC.

Inoculation 1188 was commercial product in soluble form. Freeze-dried culture of individual bacterial strains were prepared by a Pioneer contract manufacturer. Yeasts were used as freshly-grown culture: each yeast was grown overnight in MYPD broth at 28C and concentrated by centrifugation and resuspended in 10 ml water. Final cell concentrations were determined by fluorescence microscopy. Yeast suspensions prepared in this way were stable up to a week under refrigeration. The freeze-dried bacterial treatments were solubilized in sterile water before application. All treatments were applied on the forage with a 30 cc syringe fitted with a 16 gauge needle at a rate of 1ml/lb of forage for a final inoculum level of 1.0 e5 CFU/g. Table 1 summarizes the treatments used.

TABLE 1

Description of Treatments

| Treatment | Description |
|---|---|
| Control | Uninoculated |
| 1188 | Commercial Product containing *Lactobacillus plantarum* LP286, LP287, LP318, LP319, LP346, and *Enterococcus faecium* SF202 and SF301 |
| LU0211 | Experimental strain of *Lb. curvatus* |
| UL1001 | Experimental strain of *Lb. sake* |
| LU1884 | Experimental strain of *Lb. curvatus* |
| LU0211 + 1188 | Mixture of LU0211 and 1188 (50:50) |
| UL1001 + 1188 | Mixture of UL1001 and 1188 (50:50) |
| LU1884 + 1188 | Mixture of LU1884 and 1188 (50:50) |
| Yeast SE24 | Experimental strain of *Saccharomyces exiguus* |
| Yeast SE136 | Experimental strain of *Saccharomyces exiguus* |
| Yeast SE151 | Experimental strain of *Saccharomyces exiguus* |
| Yeast SE24 + 1188 | Mixture of SE24 and 1188 (50:50) |
| Yeast SE136 + 1188 | Mixture of SE136 and 1188 (50:50) |
| Yeast SE151 + 1188 | Mixture of SE151 and 1188 (50:50) |

Table 2 and FIG. 1 show that pooled result of six trials. Alone or in combination with 1188, the three yeast isolates improved aerobic stability over 1188, control and other bacterial inoculant treatments. In yeast-only treatments, pH levels were higher, lactate/acetate ratios were decreased, and ethanol levels increased as compared to treatments containing 1188 inoculant. Table 2 shows that when Yeast SE24 and SE136 were combined with 1188, the fermentation parameters of pH, lactate/acetate ratio, and ethanol were better than with yeast alone. FIG. 1 shows that aerobic stability was improved over control and 1188-alone treatments.

TABLE 2

Results from Buxtehude Grass trial: Treatment LSMeans, Day 65 (Over Cuts)

| TRT | pH | Stability (h) | Aerobic Loss (%) | Total yeast counts | Lactate-assim yeast | Lactate | Acetate | Lactate/acetate ratio | Ethanol | Butyrate |
|---|---|---|---|---|---|---|---|---|---|---|
| 1188 | 4.04 | 67 | 9.4 | 2.41E+06 | 1.18E+06 | 1.92 | 0.29 | 6.6 | 0.68 | 0.02 |
| CONTROL | 4.77 | 66 | 9.7 | 2.43E+06 | 1.17E+06 | 1.15 | 0.36 | 3.2 | 0.68 | 0.10 |
| LU0211 | 4.29 | 65 | 10.3 | 1.57E+06 | 6.09E+05 | nd | nd | nd | nd | nd |
| LU0211 + 1188 | 4.00 | 59 | 11.6 | 3.31E+06 | 1.83E+06 | nd | nd | nd | nd | nd |
| LU1884 | 4.29 | 56 | 11.1 | 2.67E+06 | 1.26E+06 | nd | nd | nd | nd | nd |
| LU1884 + 1188 | 4.02 | 52 | 12.3 | 1.08E+06 | 8.89E+05 | nd | nd | nd | nd | nd |
| UL1001 | 4.31 | 80 | 9.0 | 1.87E+06 | 3.86E+05 | nd | nd | nd | nd | nd |
| UL1001 + 1188 | 4.00 | 44 | 13.2 | 1.65E+06 | 9.58E+05 | nd | nd | nd | nd | nd |
| SE24 | 4.65 | 116 | 3.5 | 1.59E+05 | 3.10E+04 | 1.44 | 0.43 | 3.3 | 2.48 | 0.06 |
| SE136 | 4.81 | 130 | 2.3 | 3.27E+04 | 8.34E+03 | 1.28 | 0.43 | 2.8 | 2.63 | 0.06 |
| SE151 | 4.95 | 131 | 2.0 | 5.76E+05 | 3.35E+04 | 1.31 | 0.43 | 3.0 | 2.47 | 0.06 |
| SE24 + 1188 | 4.16 | 103 | 4.5 | 3.58E+05 | 2.01E+04 | 1.94 | 0.38 | 5.1 | 1.80 | 0.02 |
| SE136 + 1188 | 4.20 | 106 | 4.5 | 1.96E+05 | 8.31E+04 | 1.86 | 0.40 | 4.7 | 1.99 | 0.03 |
| SE151 + 1188 | 4.26 | 93 | 6.0 | 2.17E+06 | 7.09E+04 | 1.63 | 0.34 | 4.8 | 1.58 | 0.03 |

Example 2

Buxtehude Whole Plant Corn Silage Trials

An experiment was conducted to inoculate whole plant corn forage with yeast having "killer" activity as well as bacteria that exhibit anti-yeast activity in bench-top assays, to determine whether aerobic stability of the silage is improved.

Methods

Trials were carried out by the standard methods used in European silage research studies (see Example 3). Whole plant corn (hybrid 'Noveta') was chopped and ensiled at 28.3 to 39.5% dry matter. PVC silos 4"×14" were used with 50% compaction rate (approx. 100 kg dry matter/m3) and two 48 hr periods of air infusion at 4 and 6 weeks post-ensiling. There were four locations and two replicate silos per treatment per opening day. Bacterial and yeast inoculants were prepared as described in Example 1. Table 3 summarizes the treatments used.

TABLE 3

Description of Treatments

| Treatment | Description |
|---|---|
| Control | Uninoculated |
| 1188 | Commercial Product containing *Lactobacillus plantarum* LP286, LP287, LP318, LP319, LP346, and *Enterococcus faecium* SF202 and SF301 |
| LU0211 | Experimental strain of *Lb. curvatus* |
| UL1001 | Experimental strain of *Lb. sake* |
| LU1884 | Experimental strain of *Lb. curvatus* |
| LU0211 + 1188 | Mixture of LU0211 and 1188 (50:50) |
| UL1001 + 1188 | Mixture of UL1001 and 1188 (50:50) |
| LU1884 + 1188 | Mixture of LU1884 and 1188 (50:50) |
| Yeast SE24 | Experimental strain of *Saccharomyces exiguus* |
| Yeast SE136 | Experimental strain of *Saccharomyces exiguus* |
| Yeast SE151 | Experimental strain of *Saccharomyces exiguus* |
| SE24 + 1188 | Mixture of SE24 and 1188 (50:50) |
| SE136 + 1188 | Mixture of SE136 and 1188 (50:50) |
| SE151 + 1188 | Mixture of SE151 and 1188 (50:50) |

Results

Table 4 and FIG. 2 show the pooled result of four trials. The low pH (less than 4.3) indicated that good fermentation had occurred in all treatments. Aerobic stability of the 'anti yeast bacteria' treated silages was similar to the untreated control silage. Silage treated with the commercial product 1188 was less stable than control silage in this study. Whole plant corn silage treated with yeast alone or in combination with 1188 had 20 to 45 h higher aerobic stability than 1188 or control treatments.

TABLE 4

Results from Buxtehude Whole Plant Corn trial:
Treatment LSMeans, Day 65 (Over Cuts

| TRT | pH | Stability (h) | Aerobic Loss (%) |
|---|---|---|---|
| 1188 | 4.00 | 11.13 | 12.85 |
| CONTROL | 4.02 | 24.13 | 13.62 |
| LU0211 | 3.98 | 21.13 | 11.92 |
| LU0211 + 1188 | 3.97 | 18.75 | 12.12 |
| LU1884 | 3.92 | 25.88 | 11.60 |
| LU1884 + 1188 | 3.94 | 39.38 | 10.96 |
| UL1001 | 3.93 | 31.38 | 9.40 |
| UL1001 + 1188 | 3.94 | 17.63 | 13.19 |
| SE24 | 4.21 | 55.50 | 8.96 |

TABLE 4-continued

Results from Buxtehude Whole Plant Corn trial:
Treatment LSMeans, Day 65 (Over Cuts

| TRT | pH | Stability (h) | Aerobic Loss (%) |
|---|---|---|---|
| SE24 + 1188 | 4.22 | 67.88 | 6.03 |
| SE136 | 4.16 | 42.25 | 9.24 |
| SE136 + 1188 | 4.18 | 51.25 | 8.43 |
| SE151 | 4.22 | 51.00 | 9.34 |
| SE151 + 1188 | 4.20 | 45.13 | 9.53 |

Example 3

U.S. Grass Silage Trial

The purpose of this trial was to look at different treatments that might affect aerobic stability of grass. Yeast with "killer" activity were tested along with individual bacterial strains from the commercial product 1188.

Methods

Trials were carried out at Delevan, Wis. and Elkhorn, Wis. Ryegrass was cut and wilted to 33–34% dry matter, chopped and ensiled in model scale silos. Bacterial and yeast inoculants were prepared as described in Example 1. Treatments are summarized in Table 5.

TABLE 5

Description of Treatments

| Treatment | Description |
|---|---|
| Control | Uninoculated |
| 1188 | Commercial Product containing *Lactobacillus plantarum* LP286, LP287, LP318, LP319, LP346, and *Enterococcus faecium* SF202 and SF301 |
| SE24 | Experimental strain of *Saccharomyces exiguus* |
| LP286 | *Lactobacillus plantarum* LP286 |
| LP319 | *Lactobacillus plantarum* LP286 |
| SF202 | *Enterococcus faecium* SF202 |
| LP286 + SE24 | 50:50 mixture of LP286 and SE24 |
| LP319 + SE24 | 50:50 mixture of LP319 and SE24 |
| SF202 + SE24 | 50:50 mixture of SF202 and SE24 |

Packing

For each treatment, two 4"×14" standard PVC experimental silos were packed at approx. 230 kg DM/m3. The forage was pressed to a standard density with a hydraulic press. The silos were fitted with Fernco quick caps at each end; the top one having a Bunsen valve to allow for gas escape. After filling the silos were kept in an environmentally controlled room (approximately 72° F.) until opening.

Analyses

Four pre-ensiled uninoculated forage samples were taken while filling during each trial for pH and microbial analysis. DM was determined by drying approximately 150 g of forage for 72 hours in a 55° C. oven. pH was determined after macerating 11 g of forage with 99 ml of sterile deionized water in a stomacher. VFA analysis was done by HPLC on the filtered water extracts of the silage.

On Day 92, silos were opened, then emptied and mixed. Samples were taken for pH, DM, and aerobic stability analysis. Aerobic stability was determined by placing 2.5 lb. of silage into a plastic-lined polystyrene cooler and placing a temperature probe in the center of the silage mass. The coolers were kept in a temperature controlled room. Ambient temperature and silage temperature were measured every three hours for one week and recorded by a datalogger. The ROT value for the silage was defined as the time in hours it took for the silage temperature to rise 1.7° C. above ambient. Cumm_DD is the integration of the area between the actual temperature curve and a line drawn at the ambient temperature.

Results

Table 6 shows the pooled results of two trials. SE24 improved aerobic stability (higher ROT value, lower Cumm_DD value) in grass silage alone and in combination with two strains of *L. plantarum*. To a lesser extent, aerobic stability also was improved when SE24 was mixed with a strain of *E. faecium*. In treatments containing the yeast strains, pH values were higher and lactate/acetate ratios were lower than in 1188-treated silage at day 92. However, when SE24 was mixed with a strain of *L. plantarum*, the pH values were acceptably low for grass silage (4.5 or less)and aerobic stability was improved over 1188, control, and the *L. plantarum* treatments alone.

TABLE 6

Results of US grass silage study, Day 92.
LS Means of two locations, two silos per location.

| TRT | pH | ROT | Cumm_DD | Lactate | Acetate | Lactate/Acetate |
|---|---|---|---|---|---|---|
| 1188 | 3.97 | 76.5 | 121.8 | 0.150 | 0.012 | 13.08 |
| CONTROL | 4.03 | 67.5 | 172.9 | 0.119 | 0.012 | 10.72 |
| SE24 | 4.65 | 127.5 | 26.5 | 0.111 | 0.033 | 3.34 |
| LP286 | 3.99 | 55.5 | 149.1 | 0.198 | 0.015 | 12.99 |
| LP286 + SE24 | 4.50 | 121.5 | 39.3 | 0.111 | 0.027 | 4.12 |
| LP319 | 3.93 | 64.5 | 99.3 | 0.145 | 0.012 | 12.36 |
| LP319 + SE24 | 4.38 | 112.5 | 56.6 | 0.110 | 0.023 | 4.80 |
| SF202 | 4.01 | 52.5 | 194.3 | 0.163 | 0.014 | 11.66 |
| SF202 + SE24 | 4.59 | 87.0 | 91.9 | 0.092 | 0.023 | 3.99 |

Example 4

Protocol for Determining Aerobic Stability

DETERMINATION OF AEROBIC DETERIORATION SYSTEM VÖLKENRODE

H. Honig

The system is based on the linear correlation existing between temperature rise and intensity of CO2-production, which again can be transformed into DM-(Glucose-) losses via the respiration formula. The conversion factors given later relate to the test set-up used here. Higher insulation and larger forage amounts will give higher temperature rise at the same losses.

Containers 1 l aluminum tins, 100 mm diameter, 150 mm high, covered with plastic sheet, 10 mm diameter hole in tin bottom and covering sheet, 60 mm styrofoam insulation to the sides, 30 mm to top and bottom.

Gas flow

Gas flow is secured by the difference in specific weight of the $CO_2$, produced during the process, and the surrounding air. The hole diameter is sufficient for the necessary gas exchange as is shown by comparative measurements with the "Sapromat-system" (Compensating the O2 deficit automatically at demand). Tin cover should be plastic to avoid excessive drying of the surface layers of material.

Temperature measurement

Thermo couple connected to a 100 channel automatic printer. Measurements are taken at 6-hour intervals and averaged daily.

Basic temperature

Containers are stored in a 20° C. controlled temperature room. If material is colder at the beginning, it should be given time to adjust to 20° C. before applying insulation.

Filling quantity 100 g of DM is the basic filling quantity. As temperature rise shows a linear correlation to filling quantity in a range from 60 to 130 g DM, data can be corrected for small deviations. If material with high bulk density does not fill the 1 l volume, styrofoam disks with a center hole of 12 mm are put in as a substitute.

Loss calculation

DM content is the second factor besides filling quantity to be allowed for in the conversion from temperature rise to DM losses. The following table is based on extensive comparisons of temperature rise in the described set-up and simultaneous CO2 determinations.

DM loss, % per day at 1° C. temperature rise a) Factor FDM100 (at 100 g DM filling weight)

| % DM | 0 | 1 | 2 | 3 | 4 | 5 | 6 | 7 | 8 | 9 |
|---|---|---|---|---|---|---|---|---|---|---|
| 10 | 0.450 | 0.438 | 0.425 | 0.413 | 0.400 | 0.388 | 0.375 | 0.363 | 0.350 | 0.338 |
| 20 | 0.325 | 0.315 | 0.306 | 0.279 | 0.287 | 0.278 | 0.268 | 0.259 | 0.249 | 0.240 |
| 30 | 0.230 | 0.226 | 0.222 | 0.218 | 0.214 | 0.210 | 0.206 | 0.202 | 0.198 | 0.194 |
| 40 | 0.190 | 0.186 | 0.181 | 0.177 | 0.172 | 0.168 | 0.163 | 0.159 | 0.154 | 0.150 |
| 50 | 0.145 | 0.140 | 0.136 | 0.131 | 0.127 | 0.123 | 0.118 | 0.114 | 0.109 | 0.105 |
| 60 | 0.100 | | | | | | | | | | b) Factor FDM (at variable filling weight (60 . . . 130 g))

$$FDM = FDM100 \times \frac{100}{DM\,filling\,weight\,(g)}$$

Loss curve

The daily determined losses are accumulated and plotted versus storage time. Normal storage time in Völkenrode is 9 days.

What is claimed is:

1. A composition for use as a silage inoculant comprising:
a yeast strain selected from the group consisting of SE24, SE136, SE151, said yeast stains having ATCC accession numbers 74441, 74442, and 74443, respectively and a carrier.

2. The composition of claim 1 wherein the composition contains from about $10^2$ to about $10^{12}$ viable organisms per gram.

3. The composition of claim 1 wherein the composition contains from about $10^7$ to about $10^{10}$ viable organisms per gram.

4. The composition of claim 1 wherein the composition contains from about $10^9$ to about $10^{10}$ viable organisms per gram.

5. The composition of claim 1 wherein the carrier is a liquid.

6. The composition of claim 1 wherein the carrier is a solid.

7. The composition of claim 1 wherein said carrier is a solid carrier and is water soluble and selected from the group consisting of calcium carbonate, starch, and cellulose.

8. A method for treating animal fed or silage susceptible to the growth thereon of spoilage or organisms which comprises;
adding to said feed a yeast strain that produces antimicrobial factors that inhibit the growth of said spoilage organisms selected from the group consisting of SE24, SE136, SE151.

9. A method according to claim 8, wherein the silage is selected from the group consisting of grass, maize, alfalfa, wheat, legumes, sorghum, sunflower, and barley.

10. A method according to claim 8, wherein the inhibition of growth of spoilage organisms is added on ensiling.

11. A method according to claim 8, which comprises maintaining the silage for at least 30 days.

12. A method according to claim 8, wherein the silage is in an object or objects selected from the group consisting of a bale, an oxygen limiting bag, a bunker, a stave silo, oxygen limiting silos, bags, and piles.

13. A method according to claim 8, which comprises adding to the feed or silage a microorganism having the ability to produce antimicrobial factors that inhibit the growth of spoilage organisms on fermentation.

14. The method of claim 13 wherein said microorganism is *Saccharomyces exiguus* strain SE24 having ATCC accession number 74441.

15. The method of claim 13 wherein said microorganism is *Saccharomyces exiguus* strain SE136 having ATCC accession number 74442.

16. The method of claim 13 wherein said microorganism is *Saccharomyces exiguus* strain SE151 having ATCC accession number 74443.

17. A composition produced by the method of claim 8.

18. Animal feed to which has been added a yeast strain in accordance with the method of claim 8.

19. Animal feed to which has been added a microorganism in accordance with the method of claim 13.

20. Silage to which has been added a yeast strain in accordance with the method of claim 8.

21. Silage to which has been added a microorganism in accordance with the method of claim 13.

* * * * *

UNITED STATES PATENT AND TRADEMARK OFFICE
CERTIFICATE OF CORRECTION

PATENT NO. : 6,489,158 B1
DATED : December 3, 2002
INVENTOR(S) : Carol A. Hendrick et al.

It is certified that error appears in the above-identified patent and that said Letters Patent is hereby corrected as shown below:

Column 15,
Line 23, delete "fed" and insert -- feed --
Line 24, delete "or"

Signed and Sealed this

Fourth Day of March, 2003

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 1776
<212> TYPE: DNA
<213> ORGANISM: Yeast integration vector

<400> SEQUENCE: 1

```
ctacggaaac cttgttacga cttttagttc tctaaatga ccaagtttgt acaaattctc      60
cgctctgaga tggagttgcc ccctcctcta agcagatcct gaggcctcac taagccattc     120
aatcggtact agcgacgggc ggtgtgtaca aagggcaggg acgtaatcaa cgcaagctga     180
tgacttgcgc ttactaggaa ttcctcgttg aagagcaata attacaatgc tctatcccca     240
gcacgacgga gtttcacaag attaccaaga cctctcggcc aaggttagac tcgctggctc     300
cgtcagtgta gcgcgcgtgc ggcccagaac gtctaagggc atcacagacc tgttattgcc     360
tcaaacttcc atcggcttga aaccgatagt ccctctaaga agcggacaac cagcaaatgc     420
tagcaccact atttagtagg ttaaggtctc gttcgttatc gcaattaagc agacaaatca     480
ctccaccaac taagaacggc catgcaccac cacccacaaa atcaagaaag agctctcaat     540
ctgtcaatcc ttattgtgtc tggacctggt gagtttcccc gtgttgagtc aaattaagcc     600
gcaggctcca ctcctggtgg tgcccttccg tcaattcctt taagtttcag ccttgcgacc     660
atactccccc cagaacccaa agactttgat ttctcgtaag gtgccgagtg ggtcattaaa     720
aaaacaccac ccgatcccta gtcggcatag tttatggtta agactacgac ggyatctgat     780
catcttcgat cccctaactt tcgttcttga ttaatgaaaa cgtccttggc aaatgctttc     840
gcagtagtta gtcttcaata aatccaagaa tttcacctct gacaattgaa tactgatgcc     900
cccgaccgtc cctattaatc attacgatgg tcctagaaac caacaaaata gaaccaaacg     960
tcctattcta ttattccatg ctaatatatt cgagcaatac gcctgctttg aacactctaa    1020
ttttttcaaa gtaaaaatcc tggttcgcca agagccacaa ggacccaagg ttagccagaa    1080
ggaaaggtcc gcttgggatt ccagtacacg aaaaaatcgg accggccaaa cagacccaaa    1140
gttcaactac gagcttttta actgcaacaa ctttaatata cgctattgga gctggaatta    1200
ccgcggctgc tggcaccaga cttgccctcc aattgttcct cgttaaggta tttacattgt    1260
actcattcca attacaagac ccgaatgggc cctgtatcgt tatttattgt cactacctcc    1320
ctgaattagg attgggtaat ttgcgcgcct gctgccttcc ttggatgtgg tagccgtttc    1380
tcaggctccc tctccggaat cgaaccctta ttccccgtta cccgttgaaa ccatggtagg    1440
ccactatcct accatcgaaa gttgatagg cagaaatttg aatgaaccat cgccagcaca    1500
aggccatgcg attcgaaaag ttattatgaa tcatcaaaga gtccgaagac attgattttt    1560
tatctaataa atacatctct tccgtaaggt cgagatttta agcatgtatt agctctagaa    1620
ttaccacagt tataccatgt agtaaaggaa ctatcaaata aacgataact gatttaatga    1680
gccattcgca gtttcactgt ataaattgct tatacttaga catgcatggc ttaatctttg    1740
agacaagcat atgactactg gcaggatcaa ccaggt                                1776
```